United States Patent [19]

Stolowitz

[11] Patent Number: 4,665,037

[45] Date of Patent: May 12, 1987

[54] METHOD OF SEQUENCING PEPTIDES

[75] Inventor: Mark L. Stolowitz, Long Beach, Calif.

[73] Assignee: Analytichem International, Inc., Harbor City, Calif.

[21] Appl. No.: 857,738

[22] Filed: Apr. 28, 1986

[51] Int. Cl.[4] ...................... G01N 30/00; G01N 33/68
[52] U.S. Cl. ...................................... 436/89; 436/161; 436/178
[58] Field of Search ......................... 436/89, 161, 178; 530/345, 402, 427

[56] References Cited

U.S. PATENT DOCUMENTS

| | | | |
|---|---|---|---|
| 4,065,412 | 12/1977 | Dreyer | 436/89 X |
| 4,548,904 | 10/1985 | Kent et al. | 436/89 |
| 4,603,114 | 7/1986 | Hood et al. | 436/89 |

FOREIGN PATENT DOCUMENTS

| | | | |
|---|---|---|---|
| 0033449 | 3/1980 | Japan | 436/89 |
| 0257124 | 11/1969 | U.S.S.R. | 436/89 |

OTHER PUBLICATIONS

Inglis et al, J. of Biochem. and Biophys. Methods, vol. 4, pp. 279-285, 1981.
"Methods of Biochemical Analysis", vol. 26, edited by Dr. David Glick, pp. 234-236, published by John Wiley & Sons, Inc., 1980.

*Primary Examiner*—Barry S. Richman
*Assistant Examiner*—Robert J. Hill, Jr.
*Attorney, Agent, or Firm*—Blakely, Sokoloff, Taylor & Zafman

[57] ABSTRACT

A method of sequencing polypeptides is disclosed utilizing liquid-solid affinity chromotography. The method utilizes a reagent reactive at one position with the amino moiety of a terminal amino acid, and reactive at a second position with boronic acid. The reagent is coupled to the terminal amino acid. A scavenger molecule having a sulfhydryl group and an amine group reacts with the excess reagent and the excess scavenger and scavenger-reagent complex are removed on an immobilized organomercurial column. The terminal amino acid is cleaved from the polypeptide, and coupled to an immobilized boronic acid column. The amino acid is removed from the column and identified and the remainder polypeptide is recycled.

12 Claims, 10 Drawing Figures

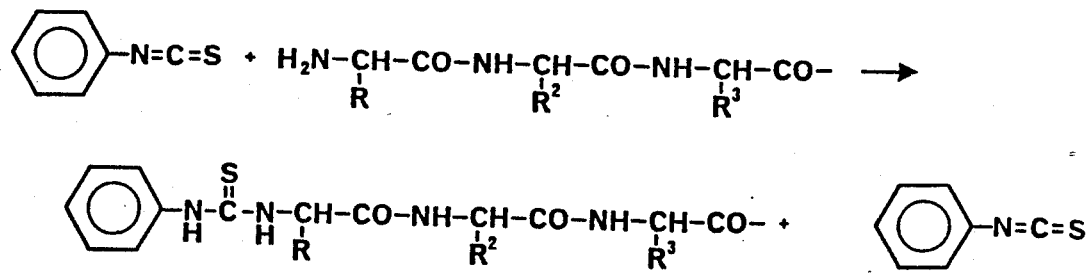
FIGURE 1B
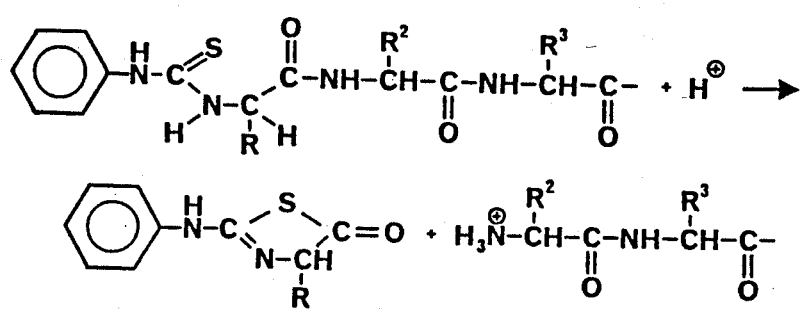
ATZ-Amino Acid
FIGURE 1C
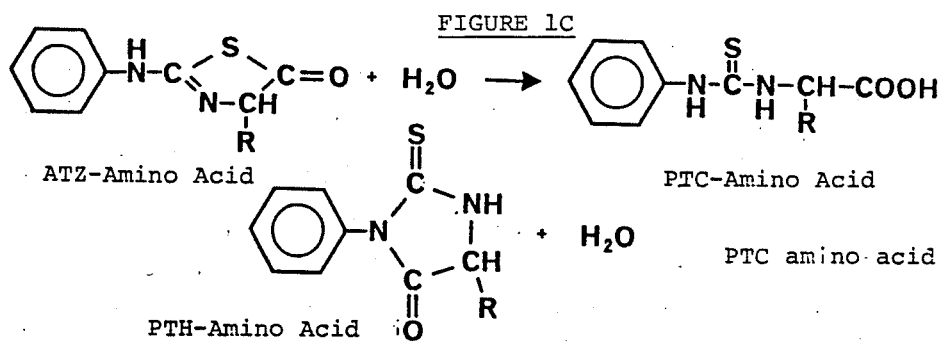
ATZ-Amino Acid                PTC-Amino Acid
PTH-Amino Acid                PTC amino acid

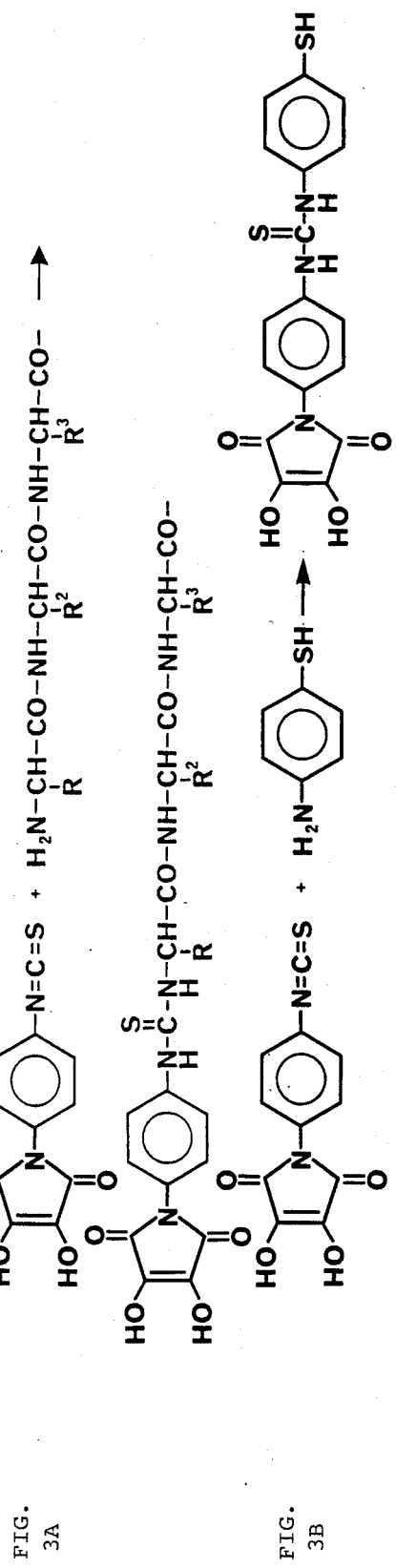
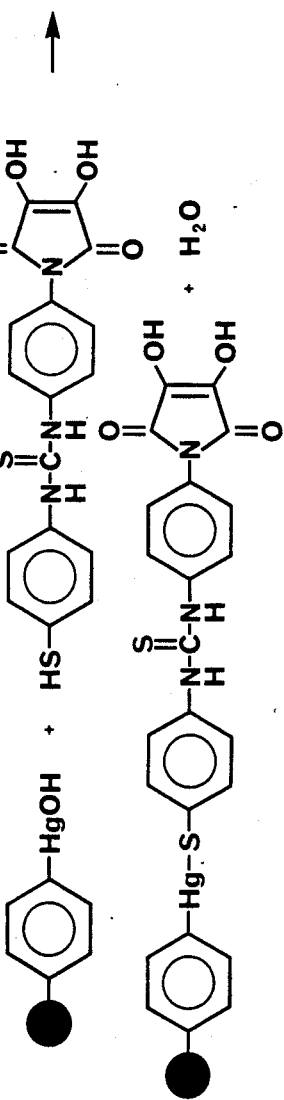
FIG. 3A
FIG. 3B
FIG. 3C
SOLID PHASE AFFINITY PEPTIDE SEQUENCING
Coupling
Covalent Chromatography

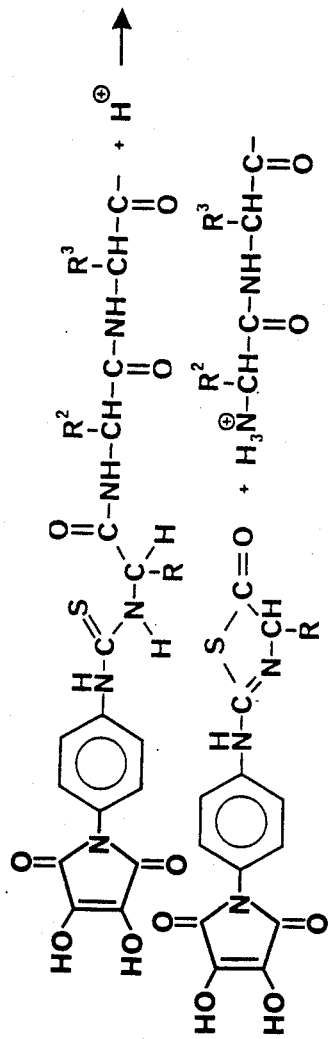
FIG. 3D Cleavage
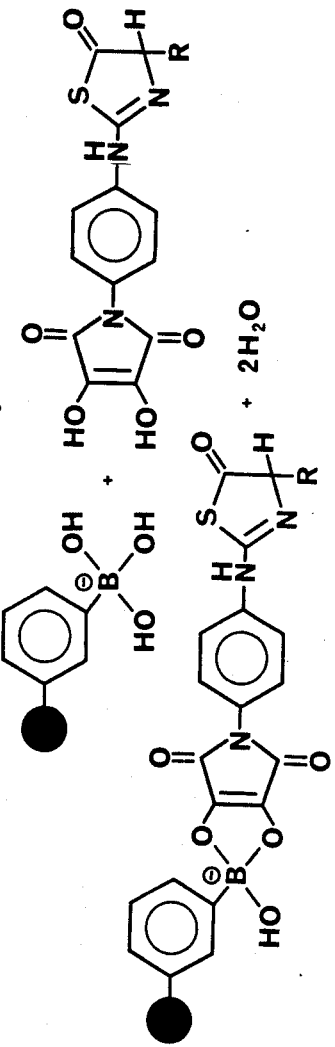
FIG. 3E Covalent Chromatography
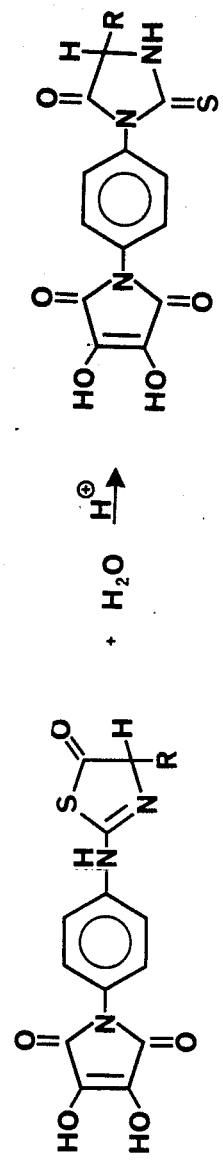
FIG. 3F Conversion

METHOD OF SEQUENCING PEPTIDES

FIELD OF INVENTION

This invention relates to a method of chemically sequencing peptides and proteins for the purpose of determining the identity and position of individual amino acids comprising the same. More specifically, the present invention relates to an improved method over the classic Edman degradation system.

BACKGROUND OF THE INVENTION

Proteins and polypeptides are naturally occuring, and recently, synthetically created, compounds that are composed of long chains of amino acids. Proteins are found throughout living things and function as hormones, structural elements, enzymes, immunoglobulins, and other constituents of living things. Research regarding the structure and functions of proteins often requires that the amino acid sequence (primary structure) of the protein, be determined. In order for a protein, or parts of a protein such as somatostatin, insulin, endorphins, etc. to be synthesized chemically or by means of recombinant DNA techniques, the sequence of amino acids comprising such protein must usually be determined before a synthesis can be attempted. In a search involving the function of proteins, such as immunoglobulins, enzymes, viral coat proteins, and cell-surface proteins, the primary structure of the protein or polypeptide must be determined in an attempt to elucidate the mechanism of action of the protein. In recominant DNA methodology, the primary structure must be determined to elucidate a corresponding structure of a DNA or RNA encoding the same.

The primary sequence of amino acids in proteins or polypeptides is commonly determined by a stepwise chemical degradation process in which single amino acids are removed one by one from the end of the polypeptide for identification. The Edman degradation is the preferred method, while other methods have been developed and can be used in certain instances. In the Edman degradation, amino acid removal from the end of the protein is accomplished by reacting the N-terminal amino acid residue with a reagent which allows selective removal of that residue from the protein. The resulting amino acid derivative is converted into a stable compound which can be chemically removed from the reaction mixture and identified.

The stepwise degradation of peptides and proteins, as proposed by Edman in the 1950's (Edman, P., Acta Chem. Scand. 4,283 (1950)) has been altered little over the past 35 years. The three step process, as shown in FIG. 1, involves coupling the N-terminal amino acid of a peptide comprising N amino acids to phenylisothiocyanate (PITC) in a solvent under alkaline or anhydrous conditions (FIG. 1A). The excess reagent (a 500 to 10,000 fold molar excess) is removed by liquid-liquid extraction, (usually in multiple steps) and the solvent is removed in vacuo. The N-terminal amino acid is then subjected to cleavage by anhydrous acid to form an anilinothiazolinone (ATZ) derivative of the amino-terminal amino acid and the salt of a free peptide of amino acid of N-1 length which is the original peptide with the terminal amino acid removed. FIG. 1B. The cleavage acid is removed in vacuo and the ATZ derivative of the amino acid is extracted from the residual peptide which remains in the aqueous phase. The ATZ amino acid, which is highly unstable, is then subsequently subjected to conversion to a more stable phenylthiohydantoin (PTH) amino acid by reaction with aqueous acid. FIG. 1C. The shortened residual peptide is (N−1 amino acids) is then treated with PITC to initiate the next cycle of degradation. The resultant PTH amino acid then identified by chromatography. The foregoing steps are repeated for each terminal amino acid in the peptide.

LIQUID PHASE MANUAL EDMAN TECHNIQUE

In the early stages of development, the Edman degradation technique was performed manually. The reaction chamber is a test tube or similar vessel, sometimes provided with a special closure to permit addition and removal of reagents under an inert atmosphere. Reagents are added with a syringe or pipette and removed by the application of vacuum or by dissolving or extracting into a solvent. During coupling the protein or peptides are dissolved into an alkaline coupling buffer. This procedure is ineffective for large proteins because they are relatively insoluble in such basic medium.

Removal of the coupling buffer and undesired side products after coupling presents many problems. One problem is this technique is that the remaining peptide derivative can dry into a gummy film from which it is difficult to remove reaction side products. Some procedures attempt to alleviate this problem by employing freeze-drying. Another very significant problem is the removal of non-volatile materials because the PITC derivative of the peptide tends to be soluble in the same solvents as such materials to be removed so that either excess PITC remains, or sample is lost. One approach is to remove the volatile reagents, leaving dried PITC-derivative and non-volatile side products. The residue is then washed with one or more solvents chosen to dissolve undesired materials more readily than the PITC-peptide. However, the materials to be removed tend to be trapped into the matrix of undissolved PITC-peptide. Another approach is to agitate the PITC-peptide and other materials while dissolved in the coupling buffer with a nonpolar solvent which will not mix with the coupling buffer. Materials more soluble in the nonpolar solvent are extracted into the same, leaving the more polar PITC-peptide in solution in the polar buffer. Nonpolar solvent can dissolve materials to form a separate layer which can be removed by pipette. However, this procedure is likely to extract some of the PITC-peptide in the nonpolar solvent. Removal of the extraction solvent without also removing some of the polar solvent and PITC-peptide and without admitting oxygen into the vessel is extremely difficult to perform.

Because the above PITC-peptide coupling procedure is carried out in a liquid phase, the coupling buffer cannot be chosen for optimum coupling characteristic. A strong base promotes coupling most effectively. However, because large quantities of water are present in the liquid phase coupling medium, the pH level must be limited to below a value at which hydrolysis of the peptide and reagent occurs. Thus, a medium at a pH level of about 9 is employed as a compromise between the desired high pH to promote coupling and a lower pH to limit hydrolytic cleavage and reagent degradation.

An anydrous cleavage acid is added to the PITC-peptide to perform the cleavage step and is thereafter removed. Volatile acid is employed which is removed by evaporation after completion of the cleavage reaction.

Thereafter, the ATZ-amino acid derivatives are removed in an extraction solvent while leaving the residual peptide behind.

Often these extractions must be performed with as little as 25 microliters of material. As discussed above, the nonspecific loss of material often results during extraction. Further, manual sequencing consequently requires considerable dexterity and practical experience. To overcome these problems, the peptide can be immobilized on a high molecular weight polymer (Polybrene) or attached covalently to an insoluble matrix and subjected to an automated degradation described below. Although automation removes many of the difficulties encountered, it is expensive and slow (maximum of one amino acid per hour).

SOLID PHASE MANUAL EDMAN PROCEDURE

A modification of the foregoing liquid phase Edman procedure is described in Schroeder, W. A., Methods in Enzymology 11, 445 (1967) and Jentsch, Jr. Proc. First Int'l Conf. on Meth. in Protein Sequence Anal. 193 (1975). Here, the protein or peptide is non-chemically deposited on a paper strip upon which it remains during the sequencing procedure. The major difference between solid phase and the liquid phase procedure described above is that the coupling base and cleavage acid are supplied by exposure of the paper strip to a stationary atmosphere of the base or acid in a gas phase in a closed container.

The above procedure is useful for degradation of large proteins and peptides since it is not necessary to dissolve the sample for reaction. Instead, the peptide is distributed on a paper strip at a high dilution to form a thin film over a large surface area. The above system requires excessivly long periods of time to carry out one cycle of degradation. A contributing factor to such long time periods is that the gas phase reagents contact the peptide solely by convention, an inefficient procedure. Also, solvent extractions and drying are carried out without agitation or other means of forced circulation.

Another disadvantage of this procedure is that it is only effective in degrading relatively small segments of peptides or proteins. It is believed that this inefficiency is due to a significant extent to mechanical and extractive losses as well as failure to protect the reactants from oxidation.

Another disadvantage of this procedure is that different solvents must be employed to extract histidine and arginine derivatives, which solvents tend to extract the peptide as well. It is believed that this is due to incomplete immobilization of the peptides on the paper wings.

SPINNING CUP AUTOMATIC SEQUENCER

Automatic protein sequencers are described in Edman, P., and Begg, G., Eur. J. Biochem. 1, 80 (1967) and in U.S. Pat. No. 3,725,010. In such sequencers, the Edman degradation is performed in the same fundamental, manner as the foregoing liquid phase technique. The primary difference is that the reactions are carried out in a film on the inside surface of the spinning cup and liquids are removed by overflowing the lip of the cup rather than by pipette or syringe. Reagents are added to the cup by a system of pumps and valves, and material are removed by vacuum evaporation or by dissolving or extracting in non-polar solvents as in the foregoing liquid phase manual Edman procedure.

The sample is maintained as a film on the inside wall of the cup. One problem of the foregoing apparatus is that it is inefficient for the sequencing of small peptides. This is because the vigorously agitated film of sample on the wall of the cup is highly susceptible to dissolution in the washing and extracting solvents which are employed to carry away excess reagents, side products, and the desired ATZ-amino acid derivatives. Thus, small peptides are dissolved or suspended in such solvents and washed out of the spinning cup before complete sequencing. In U.S. Pat. No. 3,725,010, the use of a volatile coupling buffer which can be removed by evaporation is employed. However, a liquid extraction step is employed to remove a number of non-volatile material from the peptides. In this step, relatively small peptides are extracted from the cup.

Another disadvantage of the spinning cup approach is that drying of the protein must be performed very carefully to maintain a thin film. Thus, if evaporation of solvents is attempted by immediate application of a high volume, the solution on the cup wall will boil and splatter thereby ruining the film. Thus, initial drying of the protein is performed by a gentle restricted vacuum. After the stable dried film is thus formed, drying is completed by application of successively higher volumes. If a full vacuum is not employed, some of the volatile reagents will remain on the cup wall which will combine with different reagents in other stages of the process to form insoluble salts which interfere with the degradation reaction. Such extensive drying is time-consuming and contributes substantially to the overall cycle time. Also, the system requires a high precision vacuum apparatus. Since various materials volatilized in a vacuum system combine in dead spaces to form solid salts, it is necessary to clean the system after each run for proper maintenance of the apparatus. The problem is so acute that some workers have found it necessary to completely redesign the vacuum system of the apparatus described in U.S. Pat. No. 3,725,010.

Another disadvantage of the spinning cup sequencer is that it requires precise metering of reagents and solvents into the cup to assure that the same amount is delivered on successive cycles. Otherwise, unreacted or partially reacted protein in the cup builds up in a ring that is inaccessible to further reaction to the detriment of the degradation process. Such a metering system is complex and difficult to maintain.

Another type of automatic sequencer is set forth is Laursen, R. A., Eur. J. Biochem. 20(1971). The peptide to be degraded is covalently linked to a gel-type of solid phase support contained within a tubular glass column forming a reaction chamber. All reagents and solvents are removed from the reaction column by replacement with other solvents or reagents.

A major difference of the above system in comparison to the foregoing sequencing procedures is that evaporation is not employed as a technique for removal of materials. Instead, the column is flooded with liquid throughout the entire process in order to maintain the solid support in a swollen, porous condition. The above Laursen paper suggests that the swollen polymer beads of the support limits the procedure to the sequencing of peptides which are 30 or fewer residues in length.

In Waschter, E., Machleidt, H., Hofner, H., and Otto, J., FEBS Lett. 35, 97 (1973), macroporous glass support is employed to permit sequencing of proteins and larger peptides. A major disadvantage of the above system is that only liquid reagents are employed. Thus, complete covalent linkage of the peptide to the solid support is essential. This is because the cleavage acids are excellent solvents for proteins and peptides and would wash the unbound protein or peptide from the support material. This requirement, for complete covalent linkage limits the frequency of this technique due to the peptide or protein coupling efficiency (approximately 30 to 50%). Another disadvantage is that because the gel-type supports are adversely affected by many solvents, only a limited selection of solvents is available to dissolve peptides for coupling to the supports. It is noted that such gel-type supports are most effective for retaining small peptides. Certain residues cannot be identified because of the required coupling techniques. Another disadvantage is that coupling is a lengthy tedious process.

Another major problem in the above system is that the cleavage acid must be employed as the solvent for extraction of ATZ-amino acids from the reaction column because of the high solubility of the latter in the former. The cleavage acid also extracts undersizable materials from the column which can interfere with identification of histidine and arginine. Another disadvantage of employing the cleavage acid as the ATZ-amino acid solvent is that prolonged exposure of the ATZ-amino acids causes chemical changes which interfere with conversion of the ATZ-amino acids to PTH derivatives.

Another restriction of this system is that the exchange of reagent and solvent liquids in the reaction chamber must be performed by pumping in other liquids since none can be removed by evaporation. Pumping rates are limited by column backpressure and so this exchange is relatively slow.

IDENTIFICATION OF PTH-AMINO ACIDS

A variety of isothiocyanate reagents have been prepared, so as to allow various methods of detection of the PTH amino acids which result from the degradation. PTH amino acids have been identified by thin layer chromatography (TLC), gas chromatography (GC), gas chromatography/mass spectroscopy (GC/MS), liquid chromatograph (LC) and high performance liquid chromatography (HPLC) with ultraviolet and fluorescent detection. All contemporary methods employ HPLC.

SUMMARY OF THE PRESENT INVENTION

To overcome the foregoing difficulties encountered during liquid and solid phase sequencing of peptides the process of the present invention has been developed wherein each of the liquid-liquid extractions previously employed has been replaced by a liquid-solid extraction. The solid employed is a bonded silica adsorbant which has been chemically modified by the addition of specific reactive functionalities. To exploit the invented process, a new class of isothiocyanate (ITC) reagents have been prepared which contain a functional group designed to couple with the modified bonded silica adsorbant. The invented ITC reagents and the method of synthesizing the same are the subject of a separate copending application.

In the invented process, an isothiocyanate (ITC) reagent or a derivative thereof is used having the form A-B-C, where A is a cis or co-planar 1,2 or 1,3 diol (—OH) or 1,3 hydroxy tertiary amine which may be used to react with a boronic acid moiety to form a cyclized structure (boronate ester); B is any chromophore, fluorophore or electrophore which may be identified by visible, ultraviolet, fluorescent or electrochemical procedures; and C is a chemically functional group which can be used to react with a terminal amino acid from a polypeptide resulting in a urea or thiourea linkage, and may be, but is not limited to such primary amine reactive species as the following:

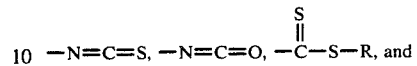
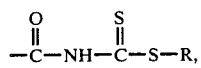

Each reagent of the foregoing class of ITC compounds will generally be referred to as the "ITC Reagent."

In the first step of the invented process, an excess amount of the ITC Reagent is added to the polypeptide or protein to be sequenced under alkaline conditions which permit a reaction between the C moiety of the ITC Reagent and the amino moiety on the N-terminal amino acid.

The extraction of excess ITC Reagent is accomplished by reaction of the excess reagent with scavenger reagent having an aromatic amine more reactive than the aliphatic N-terminal amine. This scavenger reagent also contains a sulfhydryl group which allows it to be efficiently extracted by reaction with an immobilized organomercurial matrix (PHgOH). The excess ITC-scavenger and scavenger is immobilized on a PHgOH column or slurry while the reacted ITC Reagent, remain in solution.

The remaining ITC amino acid moiety is cleaved under standard conditions known in the art for such Edman degradation reactions, generally using trifluoroacetic acid (TFA). Subsequent to the cleavage reaction, the resultant ATZ amino acid and residual peptide are dissolved in coupling buffer and the ATZ amino acid is extracted by reaction with an immobilized phenylboronic acid (PBA). The optimum conditions for this reaction are identical to those of the coupling reaction. The residual peptide is not retained on the immobilized PBA and enters the next cycle of degradation. The ATZ-amino acid is recovered from the adsorbant by acidification which also facilitates its conversion to the PTH amino acid, and which in turn, is subsequently identified by common techniques, such as HPLC.

BRIEF DESCRIPTION OF THE DRAWINGS

FIG. 1 illustrates the prior art Edman degradation.

FIG. 1A shows the step of coupling PITC to a peptide.

FIG. 1B shows the step of cleaving the n-terminal amino acid complex (ATZ-amino acid) from the peptide.

FIG. 1C shows the conversion of the ATZ-amino acid to the PTH amino acid.

FIG. 3 illustrates one cycle in the sequencing of a petide using the invented process.

FIG. 3A shows the coupling of an ITC Reagent to a peptide.

FIG. 3B shows the binding of the excess ITC reagent to a scavenger molecule for extraction.

FIG. 3C shows the extraction of excess ITC Reagent-scavenger complex using immobilized PHgOH.

FIG. 3D shows the cleavage of the ITC Reagent-peptide complex into an ATZ-amino acid and shortened peptide.

FIG. 3E illustrates the extraction of the ATZ-amino acid on a immobilized PBA column.

FIG. 3F illustrates the conversion of the ATZ-amino acid to the PTH amino acid.

DETAILED DESCRIPTION

Figure 2:
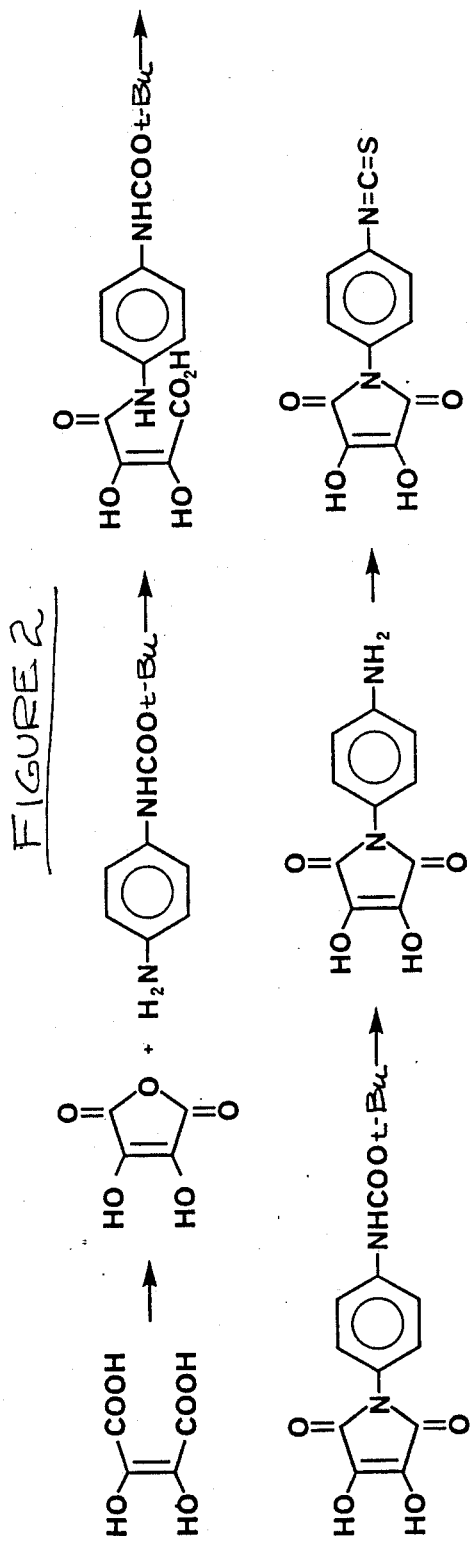
FIG. 2 illustrates the steps in the synthesis of an ITC Reagent (DHMPITC).

The present invention is a general system for the sequencing of peptides or proteins starting from the N-terminal end thereof and is effective for very small quantities of starting material.

The method comprises the following steps:

SYNTHESIS (a) Synthesis of ITC Reagent (FIG. 2).

(b) Synthesis of immobilized organomercurial compound (PHgOH).

(c) Synthesis of immobilized phenylboronic acid.

SEQUENCING (d) Coupling of ITC Reagent to N-terminal amino acid of polypeptide or protein (FIG. 3A).

(e) First extraction—removal of excess ITC Reagent.

(1) Adding to coupling reaction mixture, scavenger molecule in the form of H₂N—[]—SH to form a complex between scavenger sulfhydryl compound and excess ITC Reagent (FIG. 3B).

(2) Run reaction mixture of step e(1) over a column containing an immobilized organomercurial (PHgOH) to bind excess scavenger and ITC-scavenger complex to column, so that the polypeptide-ITC complex passes through the column unretained (FIG. 3C).

(f) Cleavage—under anhydrous acid conditions at elevated temperature for 1–30 minutes. (FIG. 3D). This reaction removes the ATZ-terminal amino acid moiety from the remainder of the peptide of protein.

(g) Second Extraction—separating the ATZ-amino acid from the remainder of the polypeptide by applying the reaction mixture of step (f) to a column containing immobilized phenylboronic acid (PBA) which binds the 1,2 or 1,3 diol or similar reactive moiety to the boronic acid (FIG. 3E).

(h) Collecting the remainder polypeptide unretained which passes through the column and subjecting the same to subsequent cycles of degradation.

(i) Removing ATZ-amino acid from PBA column in aqueous acid.

(j) Conversion of ATZ-amino acid to stable PTH amino acid.

(k) Identification of PTH-amino acid using HPLC or other standard techniques.

ITC REAGENTS

The ITC Reagents for use in the present invention have the general formula A-B-C,
where A is a cis or co-planar 1,2 or 1,3 diol (—OH) or a 1,3 hydroxyl tertiary amine which may be used to react with boronic acid under alkaline or neutral conditions;

B is any detectable chromophore, fluorophore, or electrophore detectable by under known conditions; B is used to permit localization and identification of the amino acid by the detection technique used, following separation using HPLC, GC, LC and the like; and C a chemically functional group which can be used to react with a terminal amino acid from a polypeptide resulting in a urea or thiourea linkage, and may be, but is not limited to such primary amine reactive species as the following:

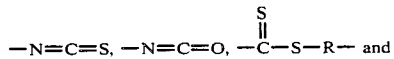

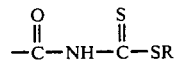

which groups are also reactive with a scavenger compounds having the general formula.

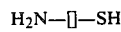

which results in a scavenger-ITC complex reactive with an organomercural moiety.

Examples of useful ITC Reagents include:

2,3-dihydroxymalemide-4'-phenylisothiocyanate (DHMPITC), shown in FIG. 2 and described below;

2,3 dihydroxy napthalene isothiocyanates;

1,8 dihydroxy napthalene isothiocyanates, dihydroxymaleimide-4'-azobenzenephenylisothiocyanate and similar compounds. Under certain conditions, a tertiary amine moiety can be used in place of one of the hydroxyls on the ITC Reagent.

The boronate ester resulting from the ITC Reagent reaction with immobilized phenylboronic acid must be sufficiently hydrolytically unstable so that the bonds between the diol, or similar reactive moiety, and the boronic acid, may be broken by hydrolysis so that the ATZ-amino acid can be eluted from the PBA column.

SCAVENGER MOLECULES

The scavenger molecules of the present invention are reacted with the excess ITC Reagent, and have the general formula H₂N—[]—SH where the [] is any relatively non-reactive alkyl or aryl group or a derivative thereof. The NH₂ group is provided to react with the N=C=S or similar reactive group on the ITC Reagent. The SH group is reactive with the PHgOH, so that the excess ITC Reagent can be removed, which has been a major problem is prior art sequencing techniques. The [] component should not be particulary reactive with any groups typically found on amino acids. Example of acceptable scavenger molecules are H₂N—Phenyl—SH (aminothiophenol), H₂N—phenyl—CH₂SH (methylmercapto)aniline), H₂N—CH₂—CH₂SH (cysteamine), and per-haloginated analogs of any of the foregoing. The particularly preferred scavengers molecule is (methylmercapto)aniline and cysteamine.

OTHER CONSIDERATIONS

In preparation for sequencing, the peptide or protein must be chemically modified to block reaction of cysteine and lysine side chains so as to prevent interaction between the cysteine side chain and the immobilized organomercurial and to prevent modification of the amino group of the lysine sidechain resulting in interaction with the immobilized boronic acid.

EXAMPLE I

Synthesis of 2,3-Dihydroxymalemide-4'-phenylisothiocyanate (DHMPITC) (FIG. 2)

3.7 grams of dihydroxyfumaric acid hydrate is dissolved in 80 milliliters of anhydrous tetrahydrofuran. A solution of 5.2 grams of 1,3-dicyclohexylcarbodiimide in 50 milliliters of tetrahydrofuran is added to the acid solution dropwise. A white solid precipitate results and is filtered from solution. The pale yellow solution containing the 2,3-dihydroxymaleic anydride is immediately employed as follows:

A solution of 5.0 grams of t-butyloxycarbonyl-1,4-phenylenediamine in 50 milliliters of tetrahydrofuran is added dropwise to the solution of 2,3-dihydroxymaleic anhydride. A deep orange solution results and is heated at approximately 50 degrees Centigrade for 4 hours. The solution is allowed to cool to room temperature and then evaporated to dryness. A reddish brown waxy material is obtained. The crude product is then dissolved in 150 milliliters of 4N hydrochloric acid in dioxane and stirred for one hour at room temperature. Purified nitrogen gas is then bubbled through the solution to remove the hydrochloric acid. The resulting heterogeneous mixture is evaporated to dryness under reduced pressure to yield a dark brown solid.

The 4'-(2,3-dihydroxymaleimide)aniline crude product is suspended in 200 milliliters of water to which is added 25 milliliters of concentrated hydrochloric acid. The resulting deep red solution is stirred while 2.3 milliliters of thiophosgene are added. The reaction is then allowed to proceed for three hours at room temperature. The crude product is filtered from solution, washed with 0.1N hydrochloric acid, taken up in chloroform and purified on a silica flash column eluted with chloroform. The first eluting product is dried under vacuum to yield 2,3-dihydroxymaleimide-4'-phenylisothiocyanate. The yield was 64%. Infrared analysis showed a strong band at 2100 cm$^{-1}$ characteristic of isothiocyanates, and a band at 3400 cm$^{-1}$ characteristic of the vicinal hydroxyls.

EXAMPLE II

Synthesis by N-Phenylmercury-N'-propylsilylurea Silica (PHgOH)

Aminopropyl silica gel (1.5% N), 40 uM irregular with 60 A average porosity, was dried at 80° C. for three hours then allowed to cool to room temperature in a desiccator. For each gram of aminopropyl silica gel, 0.8 grams of N,N'-carbonyldiimidazole and 0.13 milliliters of triethylamine are dissolved in 10 milliliters of methylene chloride. The aminopropyl silica gel is added to the reaction mixture and stirred for three hours at room temperature. The activated silica gel is filtered from solution and washed with methylene chloride and twice with dimethylsulfoxide (DMSO). The activated silica gel is then immediately added to a solution of 10% p-aminophenylmercuric acetate in DMSO. For each gram of activated silica gel, 7 milliliters of solution is employed. The reaction mixture is stirred for 24 hours 40° C. The modified silica gel is then returned to a solution of ammonia saturated DMSO and the reaction mixture stirred for 3 hours at room temperature. Finally, the product is filtered from solution and washed with 50% DMSO: water, 0.02N hydrochloric acid, 1N sodium chloride and twice with water. The product is then allowed to dry to room temperature.

EXAMPLE III

Synthesis of N-Phenylboronic acid-N'-propylsilylurea Silica (PBA)

Aminopropyl silica gel (1.5% N), 40 uM irregular with 60 A average porosity, was dried at 80° C. for three hours then allowed to cool to room temperature in a desiccator. For each gram of aminopropyl silica gel, 0.8 grams of N,N'-carbonyldiimidazole and 0.13 milliliters of triethylamine are dissolved in 10 milliliters of methylene chloride. The aminopropyl silica gel is added to the reaction mixture and stirred for three hours at room temperature. The activated silica gel is filtered from solution and washed with methylene chloride and twice with dimethylsulfoxide (DMSO). The activated silica gel is then immediately added to a solution of 5.3% p-amino phenylboronic acid hemisulfate in 90% DMSO. For each gram of activated silica gel, 7 milliliters of solution is employed. The reaction mixture is stirred for 24 hours 40 degrees C. The modified silica gel is then returned to a solution of ammonia saturated DMSO and the reaction mixture stirred for 3 hours at room temperature. Finally, the product is filtered from solution and washed with 50% DMSO, water, 0.02N hydrochloric acid, 1N sodium chloride and twice with water. The product is then allowed to dry to room temperature.

EXAMPLE IV

Use in Sequencing 2,3-dihydroxymaleimide-4'-phenylisothiocyanate (DHMPITC) (Example I) was dissolved in acetonitrile at a concentration of 5% (w/v). The peptide Angiotensin 1, 50 nanomoles was dissolved in 200 microliters of solid phase sequencing buffer (3:2 pyridine:N-methylmorpholine trifluoroacetate, pH 8.2) and transferred to a 1 milliliter reaction vial. 20 micoliters of DHMPITC solution was added. The vial was purged with nitrogen and heated at 50 degrees Centigrade for 15 minutes. 50 microliters of a solution of 5% (v/v) (methylmercapto)aniline was subsequently added to the reaction vial and heating continued for an additional 15 minutes. The vial was then removed from the heater and the contents dried under vacuum at 50 degrees C. for 10 minutes.

A 100 milligram column of N-Phenylmercury-N'-propylsilylurea silica (PHgOH) (Example II) measuring 4 millimeters internal diameter was prepared by washing with methanol, water and 200 millimolar trimethylammonium acetate buffer, pH 6.8. The dry contents of the reaction vial were taken up in 500 microliters of 3:2 trimethylammonium acetate, pH 6.8:dioxane buffer and applied to the PHgOH column. The column was eluted by aspiration and washed with an additional 500 microliters of the aforementioned buffer. The effluents were combined and dried under vacuum at 50 degrees Centigrade for 30 minutes.

To the dry residue in the reaction vial, free of excess DHMPITC and (methylmercapto)aniline and containing the 2,3-dihydroxy-maleimide-4'-phenylthiocarbamyl peptide, was added 250 microliters of anhydrous trifluoroacetic acid and the vial was heated to 50 degrees Centigrade for 10 minutes. The contents of the vial were then dried under vacuum for 10 minutes at 50 degrees Centigrade.

A 100 mg column of N-Phenylboronic acid-N'-propylsilylurea silica (PBA) (Example III) measuring 4 millimeters internal diameter was prepared by washing with methanol, water and 50 millimolar triethylammonium acetate buffer, pH 8.2. The dry contents of the reaction vial were taken up in 500 microliters of 1:1 triethylammonium acetate, pH 8.2:acetonitrile buffer and applied to the PBA column. The residual peptide was eluted from the column by aspiration and the column was washed with an additional 500 microliters of the aforementioned buffer. The efluents were combined, dried under vacuum and subjected to the next cycle of sequencing.

The 2,3-dihydroxymaleimide-4'-anilinothiazolinone amino acid was eluted from the PBA column with 500 microliters of 5:3:2 acetonitrile:water:trifluoracetic acid and heated at 85 degrees Centigrade for 15 minutes to effect cyclization to the corresponding phenylthiohydantoin.

The resulting 2,3-dihydroxy-4'-phenylthiohydantoins were identified by reverse phase high performance liquid chromatography (HPLC) on a octadecyl column measuring 4.6×150 millimeters. The retention times associated with the DHMPTH amino acids were determined by gradient elution with acetonitrile (up to 40% (v/v) added to an aqueous buffer of 0.15% (v/v) trifluoroacetic acid. Fluorescence detection was employed in connection with ultraviolet detection.

I claim:

1. A method for determining the identity of an N-terminal amino acid of a polypeptide comprising:
    (a) providing a coupling reagent comprising an isothiocyanate or a derivative thereof having the form A-B-C, where the A moiety is a cis or co-planar 1,2 or 1,3 diol or 1,3 hydroxy tertiary amine, the B moiety is any chromophore, fluorophore or electrophore which may be identified by visible, ultraviolet, fluorescent or electrochemical procedures, and the C moiety is a functional group which reacts with an N-terminal amino acid of a polypeptide to form a urea or thiourea linkage;
    (b) forming a reaction mixture by contacting a sample of a polypeptide with the coupling reagent such that the C moiety of the coupling reagent reacts with the N-terminal amino acid of the polypeptide to form a coupling reagent polypeptide complex;
    (c) removing excess coupling reagent from the reaction mixture by reacting excess coupling reagent with a scavenger molecule to form a scavenger molecule complex, contacting the reaction mixture with a first immobilized reagent to bind excess scavenger molecule and the scavenger molecule complex thereto, and removing the coupling reagent polypeptide complex from contact with the first immobilized reagent;
    (d) cleaving the coupling reagent polypeptide complex to form a mixture of a cleaved polypeptide and a complex comprising the coupling reagent and the N-terminal amino acid of the polypeptide;
    (e) separating the cleaved polypeptide from the coupling reagent N-terminal amino acid complex by contacting the mixture with a second immobilized reagent which reacts with the A moiety of the coupling reagent so as to bind the coupling reagent N-terminal amino acid complex thereto and removing the cleaved polypeptide from contact with the second immobilized reagent;
    (f) converting the coupling reagent N-terminal amino acid complex to a stable compound; and
    (g) identifying the stable compound formed in step f.

2. The method of claim 1 further comprising sequencing the polypeptide by repeating the steps of claim 1 on the cleaved polypeptide from step e.

3. The method of claim 1 wherein the second immobilized reagent comprises an immobilized boronic acid.

4. The method of claim 3 wherein the immobilized boronic acid is phenylboronic acid bound to a silica gel.

5. The method of claim 4 wherein step e further comprises treating the immobilized boronic acid with aqueous acid to remove the bound coupling reagent N-terminal amino acid complex therefrom.

6. The method of claim 3, 4, or 5 wherein the immobilized boronic acid is disposed in a column.

7. The method of claim 1 wherein the scavenger molecule has the formula $H_2N-[]-SH$, where [] is an alkyl or aryl group or a perhaloginated derivative thereof, the first immobilized reagent comprises an immobilized organomercurial, and the scavenger molecule complex is formed by a reaction between the $NH_2$ moiety of the scavenger molecule and the C moiety of excess coupling reagent.

8. The method of claim 7 wherein the immobilized organomercurial comprises phenylmercury hydroxide bound to a silica gel.

9. The method of claim 7 wherein the scavenger molecule is selected from the group consisting of $H_2N$—phenyl-SH, $H_2N$—phenyl—$CH_2SH$, $H_2N$—$CH_2$—$CH_2SH$ and perhalogenated derivatives thereof.

10. The method of claim 9 wheren the scavenger molecule is (methylmercapto)aniline.

11. The method of claim 7, 9, 10, or 8 wherein the immobilized organomercurial is disposed in a column.

12. A method or determining the identity of an N-terminal amino acid of a polypeptide comprising:
    (a) providing a coupling reagent comprising 2,3-dihydroxymaleimide-4'-phenylisothiocyanate (DHMPITC);
    (b) forming a reaction mixture by contacting a sample of a polypeptide with the coupling reagent such that the isothiocyanate moiety of the coupling reagent reacts with the N-terminal amino acid of the polypeptide to form a coupling reagent polypeptide complex:
    (c) adding a (methylmercapto)aniline to the reaction mixture such that excess coupling reagent reacts with the (methylmercapto)aniline to form a scavenger molecule complex;
    (d) eluting the reaction mixture of step c over a column containing N-Phenylmercury-N'-propylsilylurea Silica (PHgOH) to bind excess (methylmercapto)aniline and the scavenger molecule complex thereto and form an effluent containing the coupling reagent polypeptide complex;
    (e) cleaving the coupling reagent polypeptide complex in the effluent of step d under anhydrous acidic conditions to form a mixture of a cleaved polypeptide and a complex comprising the coupling reagent and the N-terminal amino acid of the polypeptide;
    (f) eluting the mixture of step e over a column containing N-Phenylboronic acid-N'-propylsilylurea Silica (PBA) to bind the coupling reagent N-terminal amino acid complex and form an effluent containing the cleaved polypeptide;

(g) eluting the bound coupling reagent N-terminal amino acid complex from step f off the column containing PBA under aqueous acidic conditions to form an effluent containing the coupling reagent N-terminal amino acid complex:

(h) converting the coupling reagent N-terminal amino acid complex in the effluent of step g to a stable phenylhydantoin amino acid derivative; and (i) identifying the stable phenylhydantoin amino acid derivative formed in step h.

* * * * *